United States Patent [19]

Bollag et al.

[11] 4,316,983

[45] Feb. 23, 1982

[54] NEOPLASMIC COMPOUNDS: SUGAR ESTERS AND GLYCOSIDES

[75] Inventors: Werner Bollag, Basel; Pierre-Charles Wyss, Muttenz, both of Switzerland

[73] Assignee: Hoffmann-La Roche Inc., Nutley, N.J.

[21] Appl. No.: 158,678

[22] Filed: Jun. 12, 1980

[30] Foreign Application Priority Data

Jun. 21, 1979 [CH] Switzerland ................ 5808/79

[51] Int. Cl.³ .................. C07H 15/20; C07H 13/08
[52] U.S. Cl. .................................. 536/4; 536/115; 536/119; 536/53
[58] Field of Search .............. 536/4, 18, 115, 120, 536/53, 119; 424/180

[56] References Cited

U.S. PATENT DOCUMENTS 3,629,238 12/1971 Arasaki et al. ................ 536/4
4,089,606 5/1978 Furuya et al. ................ 536/4
4,193,931 3/1980 Loeliger .

FOREIGN PATENT DOCUMENTS 7121529 6/1971 France .

OTHER PUBLICATIONS

Noller, "Chemistry of Organic Compounds", 3rd Ed., 1965, W. B. Sanders Co., Phila., PA, pp. 402-404.
Chemical Abstracts, vol. 93, Abst. No. 186020e, 1980.

*Primary Examiner*—Blondel Hazel
*Attorney, Agent, or Firm*—Jon S. Saxe; George M. Gould; John B. Wilson

[57] ABSTRACT

The invention relates to novel sugar esters and glycosides especially derivatives of D-glucopyranoside and D-glucopyranaronate suitable for the treatment of neoplasms, acne, psoriasis and dermatoses.

9 Claims, No Drawings

NEOPLASMIC COMPOUNDS: SUGAR ESTERS AND GLYCOSIDES

BACKGROUND AND SUMMARY OF INVENTION

The compounds of the invention and the pharmaceutically acceptable acid-addition salts thereto relate to and are useful as active ingredients for pharmaceuticals, especially for topical administration. Similar compounds have been used in the treatment of acne and psoriasis, as well as for inflammatory and allergic dermatoses. The compounds of the invention are useful in such treatments and are distinguished in particular by a good tolerance, for example by the absence of skin irritations on topical administration.

The compounds of the invention have the general formula:

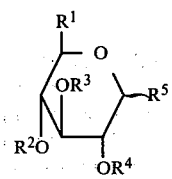

wherein $R^1$ represents a group of the formula —CH$_2$OH, —CH$_2$OR$^6$, —COR$^7$ or —CONH$_2$; $R^2$ represents hydrogen or lower alkanoyl; $R^3$ and $R^4$ represent hydrogen or lower alkanoyl or a group $R^6$; $R^5$ represents lower alkoxy or a group OR$^6$ or OR$^8$; $R^6$ represents p-[2-(5,6,7,8-tetrahydro-5,5,8,8-tetramethyl-2-naphthyl)propenyl]-benzoyl; $R^7$ represents hydroxy, lower alkoxy or OM in which M represents a cation; and $R^8$ represents p-[2-(5,6,7,8-tetrahydro-5,5,8,8-tetramethyl-2-naphthyl)-propenyl]benzyl, provided that (i) $R^1$ represents a group of the formula —CH$_2$OR$^6$, $R^2$ represents hydrogen and one of $R^3$ and $R^4$ represents hydrogen and the other represents a group $R^6$ when $R^5$ represents lower alkoxy; (ii) $R^1$ represents a group of the formula —COR$^7$ and $R^2$, $R^3$ and $R^4$ represent lower alkanoyl when $R^5$ represents a group of the formula OR$^6$; or (iii) $R^1$ represents a group of the formula —CH$_2$OH, —COR$^7$ or —CONH$_2$ and $R^2$, $R^3$ and $R^4$ represent hydrogen or lower alkanoyl when $R^5$ represents a group of the formula OR$^8$.

DETAILED DESCRIPTION OF THE INVENTION

The present invention relates to novel sugar esters and glycosides of general formula I:

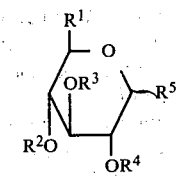

wherein $R^1$ represents a group of the formula —CH$_2$OH, —COR$^7$ or —CONH$_2$; $R^2$ represent hydrogen or lower alkanoyl; $R^3$ and $R^4$ represent hydrogen or lower alkanoyl or a group $R^6$; $R^5$ represents lower alkoxy or a group of the formula OR$^6$ or OR$^8$; $R^6$ represents a group of the formula

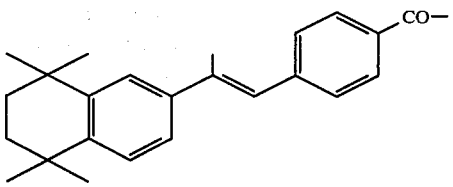

$R^7$ represents hydroxy, lower alkoxy or OM in which M represents a cation; and $R^8$ represents a group of the formula

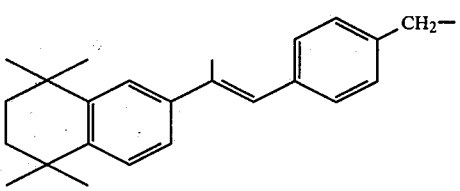

provided that: (i) $R^1$ represents a group of the formula —CH$_2$OR$^6$, $R^2$ represents hydrogen and one of $R^3$ and $R^4$ represents hydrogen and the other represents a group $R^6$ when $R^5$ represents lower alkoxy; (ii) $R^1$ represents a group of the formula —COR$^7$ and $R^2$, $R^3$ and $R^4$ represent lower alkonyl when $R^5$ represents a group of the formula OR$^6$; or (iii) $R^1$ represents a group of the formula —CH$_2$OH, —COR$^7$ or —CONH$_2$ and $R^2$, $R^3$ and $R^4$ represent hydrogen or lower alkanoyl when $R^5$ represents a group of the formula OR$^8$.

The invention also relates to the pharmaceutically acceptable acid-addition salts of formula I as well as to a process for producing the compounds of formula I and pharmaceutical preparations containing the compounds of formula I.

A preferred group of compounds of formula I comprises compounds of general formula Ia:

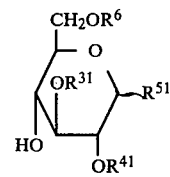

wherein $R^{51}$ represents a lower alkoxy and one of $R^{31}$ and $R^{41}$ represent a group $R^6$ as hereinbefore defined and the other represents hydrogen.

The compounds of formula Ia wherein $R^{51}$ represents methoxy, especially α-methoxy, are of particular interest.

Another preferred group of compounds of formula I comprises compounds of general formula Ib:

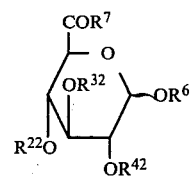

wherein $R^{22}$, $R^{32}$ and $R^{42}$ represent lower alkanoyl and $R^6$ and $R^7$ are as defined earlier.

Of the compounds of formula Ib, those in which $R^7$ represents methoxy are especially preferred.

A further aspect of the present invention is concerned with compounds of general formula Ic:

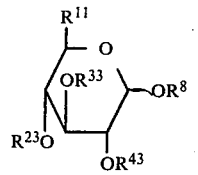

wherein $R^{11}$ represents a group of the formula $-CH_2OH$, $-COR^7$ or $-CONH_2$; $R^{23}$, $R^{33}$, $R^{43}$ represent hydrogen or lower alkanoyl and $R^8$ is as defined earlier.

Of the compounds of formula Ic, those in which $R^{11}$ represents a group of the formula $-CONH_2$ or $-COONa$ and $R^{23}$, $R^{33}$ and $R^{43}$ represent hydrogen are especially preferred.

The expression "lower" is used herein to mean groups which preferably contain from 1 to 7 carbon atoms. Examples of lower alkanoyl groups include acetyl, propionyl, butyryl and the like. Examples of lower alkoxy groups include methoxy, ethoxy, propoxy, butoxy and the like. The cation contained in the group $R^7$ as represented by M is preferably an alkali metal cation, especially the sodium cation.

As used herein the term "pharmaceutically acceptable salts" includes non-toxic salts such as those from acids selected from a group consisting of inorganic mineral acids such as hydrochloride, hydrobromide, phosphate, sulphate, nitrate and the like; or from organic acids such as acetate, formate, maleate, fumerate, benzoate and the like.

The foregoing novel sugar esters and glycosides can be produced, for example, by introducing the group $R^6$ or $R^8$ into sugar derivatives which contain free hydroxy groups in the corresponding positions, and if desired, subsequently transforming functional groups.

In particularly the compounds of formula I can be produced preferably in accordance with the invention by the following embodiments designated a,b, and c:

(a) reacting a compound of general formula II or II-1:

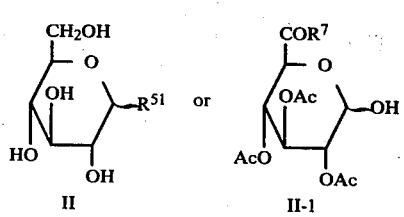

wherein $R^7$ is as defined earlier, $R^{51}$ represents lower alkoxy, and Ac represents acetyl, with an acid of the general formula $R^6OH$ wherein $R^6$ is as defined previously or with a reactive derivative thereof in the presence of a water-binding or acid-binding agent, or (b) deacetylating a compound of general formula III:

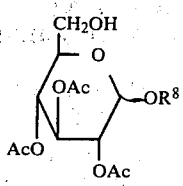

wherein $R^8$ and Ac are as defined earlier, or (c) treating a compound of general formula IV:

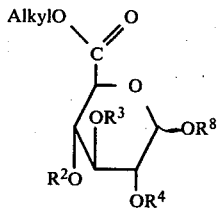

wherein $R^2$, $R^3$, $R^4$ and $R^8$ are as defined earlier, and alkyl represents straight, branched or cyclic group with from 1 to 7 carbon atoms, with methanolic ammonia, and, if desired converting a compound of formula I obtained in which $R^1$ represents lower alkoxy-carbonyl into a compound of formula I in which $R^1$ represents carboxyl or into a salt of such a compound.

Various art recognized pharmacologically reactive derivatives of the acids of formula $R^6$ may be employed in this process. Among the reactive derivatives that may be employed are the halides which are preferred. Especially preferred are the chlorides.

The reaction in accordance with embodiment (a) of the process is conveniently carried out in an inert solvent. Examples of such solvents are ethers (e.g. diethyl ether, tetrahydrofuran and dioxan), water of mixtures thereof. Examples of acid-binding agents which are suitable in this reaction are organic bases such as pyridine, or art recognized homologues thereof and inorganic bases such as alkali metal carbonates. The reaction is conveniently carried out at temperatures of 0° C. to room temperature. An exemplary water-binding agent suitable in this reaction is dicyclohexylcarbodiimide.

The deacetylation in accordance with embodiment (b) of the process can be carried out by treatment with bases such as alkali metal alkoxides (e.g. sodium methoxide in methanol). This deacetylation can be carried out at room temperature.

Embodiment (c) of the process can be carried out by treating a compound of formula IV with methanolic ammonia at room temperature.

The conversion of a lower alkoxycarbonyl group $R^1$ in a compound of formula I into the carboxyl group or a carboxylate group can be carried out by saponification, for example with an alkali such as alcoholic alkali hydroxides. A thus-obtained salt can be converted into the free acid by neutralization, for example with cation exchangers in the hydrogen ion form.

The starting materials can be prepared as described in the Examples or in an art recognized analogy thereto.

The tumour-inhibiting activity of the compounds of formula I was tested in mice in which papilloma of the skin had been induced by treatment with dimethylbenzanthracene and croton oil. A regression of the papillomae was observed after administration of the compounds of formula I. The test results are compiled in Table I, wherein:

A: p-[(E)-2-(5,6,7,8-tetrahydro-5,5,8,8-tetramethyl-2-naphthyl)-propenyl]-benzyl-β-D-glucopyranoside.
B: p-[(E)-2-(5,6,7,8-tetrahydro-5,5,8,8-tetramethyl-2-naphthyl)-propenyl]-benzyl-β-D-glucopyranoside-uronamide.
C: Sodium p-[(E)-2-(5,6,7,8-tetrahydro-5,5,8,8-tetramethyl-2-naphthyl)-propenyl]-benzyl-β-D-gluropyranoside-uronate.
D: Methyl 2,6-bis-O-[p-[(E)-2-(5,6,7,8-tetrahydro-5,5,8,8-tetramethyl-2-naphthyl)-propenyl]-benzoyl]-α-D-glucopyranoside.
E: Methyl 3,6-bis-O-[p-[(E)-2-(5,6,7,8-tetrahydro-5,5,8,8-tetramethyl-2-naphthyl)-propenyl]-benzoyl]-α-D-glucoyranoside.
F: Methyl 2,3,4-tri-O-acetyl-1-O-[p-[(E)-2-(5,6,7,8-tetrahydro-5,5,8,8-tetramethyl-2-naphthyl)-propenyl]-benzoyl]-α-D-glucopyranuronate.
G: Methyl 2,3,4-tri-O-acetyl-1-O-[p-[(E)-2-(5,6,7,8-tetrahydro-5,5,8,8-tetramethyl-2-naphthyl)-propenyl]-benzoyl]-β-D-glucopyranuronate.

TABLE 1

| Compound | Dosage | Decrease of the diameter of the papillomae (%) |
|---|---|---|
| A | 0.1 | −22 |
| B | 6 | −33 |
| C | 1.5 | −38 |
| D | 0.75 | −57 |
| E | 0.4 | −69 |
| F | 0.1 | −25 |
| G | 0.1 | −57 |

The compounds of formula I can be used as medicaments; for example, in the form of pharmaceutical preparations. The preparations for systemic administration can be manufactured, for example, by adding a compound of formula I as the active ingredient to non-toxic, inert, solid or liquid carriers which are customary per se in such preparations. The preparations can be administered enterally or parenterally. Suitable preparations for enternal administration are, for example, tablets, capsules, dragees, syrups, suspensions, solutions and suppositories. Preparations in the form of infusion or injection solutions are suitable for parenteral administration.

The dosages in which the compounds of formula I are administered can vary depending on the mode of use and route of administration as well as according to the requirements of the patients.

The compounds of formula I can be administered in amounts of ca. 0.01 mg to ca 5 mg daily in one or more dosages. Capsules containing ca 0.1 mg to ca 1.0 mg of active ingredient are a preferred dosage form.

The pharmaceutical preparations can contain inert or pharmacodynamically active additives. Tablets or granula, for example, can contain a series of binders, fillers, carriers or diluents. Liquid preparations can, for example, take the form of a sterile solution which is miscible with water. Capsules can contain, in addition to the active ingredient, a filler or thickener. Furthermore, flavour-improving additives as well as the usual substances used as preserving, stabilizing, moisturizing and emulsifying agents, salts for varying the osmotic pressure, buffers and other additives can also be present.

The previously mentioned carriers and diluents can be organic or inorganic substances (e.g. water, gelatin, lactose, starch, magnesium stearate, talc, gum arabic, polyalkyleneglycols and the like). It is, of course, prerequisite that all adjuvants used in the manufacture of the pharmaceutical preparations are non-toxic.

For topical administration the compounds of formula I conveniently used in the form of salves, tinctures, creams, solutions, lotions, sprays, suspensions and the like. Salves, creams and solutions are preferred. These preparations for topical administration can be manufactured by mixing the compounds of formula I as the active ingredient with non-toxic, inert, solid or liquid carriers which are customary per se in such preparations and suitable for topical administration.

For topical administration there are conveniently used ca 0.01% to ca 0.3%, preferably 0.02% to 0.1%, solutions, and ca 0.05% to ca 5%, preferably ca 0.05% to ca 1%, salves or creams.

If desired, an antioxidant (e.g. tocopherol, N-methyl-γ-tocopheramine, butylated hydroxyanisole or butylated hydroxytoluene) can be incorporated in the present pharmaceutical preparations.

The following Examples further illustrate the present invention but are not meant to limit the invention in scope or spirit.

EXAMPLE 1

A solution of 3.4 g of methyl 2,3,4-tri-O-acetyl-α-D-glucopyranuronate in 40 ml of pyridine was reacted at 0° C. with a solution of p-[(E)-2-(5,6,7,8-tetrahydro-5,5,8,8-tetramethyl-2-naphthyl)-propenyl]-benzoyl chloride in 70 ml of ether. The mixture was stirred at room temperature overnight, evaporated to dryness and the residue was chromatographed on silica gel with hexane/ethyl acetate. There was obtained methyl 2,3,4-tri-O-acetyl-1-O-[p-[(E)-2-(5,6,7,8-tetrahydro-5,5,8,8-tetramethyl-2-naphthyl)-propenyl]-benzoyl]-D-glucopyranuronate as a mixture of the β- and α-anomers (ca 4:1). Melting point 149°–150° C. (from ethanol); $[\alpha]_D^{25} = 3°$ (c=1 in chloroform).

The acid chloride used as the starting material can be prepared as follows:

p-[(E)-2-(5,6,7,8-tetrahydro-5,5,8,8-tetramethyl-2-naphthyl)-propenyl]-benzoic acid ethyl ester is saponified with aqueous-ethanolic potassium hydroxide at 55° C. for 18 hours to give the corresponding carboxylic acic which is converted into the acid chloride using thionyl chloride in pyridine and N,N-dimethylformamide.

EXAMPLE 2

A mixture of 3.5 g of p-[(E)-2-(5,6,7,8-tetrahydro-5,5,8,8-tetramethyl-2-naphthyl)-propenyl]-benzoic acid, 1.05 g of N,N'-dicyclohexylcarbodiimide and 0.65 g of 4-dimethylaminopyridine in 450 ml of dichloromethane was held at room temperature for 5 hours. The dicyclohexylurea was filtered off, the filtrate was treated with 1.7 g of methyl 2,3,4-tri-O-acetyl-α-D-glucopyranuronate, 1.05 g of N,N'-dicyclohexylcarbodiimide and 0.65 g of 4-dimethylaminopyridine and left to stand at room temperature overnight. The mixture was then filtered, the filtrate was evaporated and the residue was chromatographed. There was obtained a mixture of the α- and β-anomers (ca 3:2) which were separated by chromatography on a silica gel column (Merck, hexane/ethyl acetate). There was obtained methyl 2,3,4-tri-O-acetyl-1-O-[p-[(E)-2-(5,6,7,8-tetrahydro-5,5,8,8-tetramethyl-2-naphthyl)-propenyl]-benzoyl]-α-D-glucopyranuronate, melting point 172° C. (from ethanol), $[\alpha]_D^{25} = +104.1°$ (c=1 in chloroform), and the corresponding β-anomer, melting point 161° c. (from ethanol), $[\alpha]_D^{25} = -24.6°$ (c=1 in chloroform).

EXAMPLE 3

A solution of 100 mmol of p-[(E)-2-(5,6,7,8-tetrahydro-5,5,8,8-tetramethyl-2-naphthyl)-propenyl]-benzoyl chloride in 450 ml of ether was added while stirring at 0° C. over a period of 1 hour to a solution of 19.5 g of methyl α-D-glucopyranoside in 500 ml of pyridine. The mixture was stirred at 0° C. for a further 4 hours and at room temperature for 16 hours and then evaporated to dryness. The residue was dissolved in ethyl acetate and the extract was washed with 3 N hydrochloric acid, water, saturated aqueous sodium bicarbonate solution and water. After drying over sodium sulphate, the organic phase was evaporated and the residue was chromatographed on silica gel (hexane/ethyl acetate) to give methyl 2,6-bis-O-[p-[(E)-2-(5,6,7,8-tetrahydro-5,5,8,8-tetramethyl-2-naphthyl)-propenyl]-benzoyl]-α-D-glucopyranoside, melting point 203°-204° C. (from ethyl acetate), $[\alpha]_D^{25} = +27.4°$ (c=1 in chloroform), and methyl 3,6-bis-O-[p-[(E)-2-(5,6,7,8-tetrahydro-5,5,8,8-tetramethyl-2-naphthyl)-propenyl]-benzoyl]-α-D-glucopyranoside, melting point 128°-129° C. (with decomposition, from methanol), $[\alpha]_D^{25} = +135°$ (c=1 in chloroform).

EXAMPLE 4

A solution of 3.9 g of p-[(E)-2-(5,6,7,8-tetrahydro-5,5,8,8-tetramethyl-2-naphthyl)-propenyl]-benzyl-2,3,4,6-tetra-O-acetyl-β-D-glucopyranoside in 150 ml of 0.1 N sodium methoxide in methanol was held at room temperature for 30 minutes, neutralised with Amberlite IR-120 cation exchanger (hydrogen ion form) and evaporated. Recrystallisation from 2-propanol yielded p-[(E)-2-(5,6,7,8-tetrahydro-5,5,8,8-tetramethyl-2-naphthyl)-propenyl]-benzyl-β-D-glucopyranoside, melting point 156°-157° C.; $[\alpha]_D^{25} = -23.8°$ (c=1 in pyridine).

The starting material was prepared as follows:

5,6,7,8-Tetrahydro-5,5,8,8-tetramethyl-naphthalene is reacted with acetyl chloride and aluminium chloride in nitrobenzene to give (5,6,7,8-tetrahydro-5,5,8,8-tetramethyl-2-naphthyl) methyl ketone. Reduction of this ketone with lithium aluminium hydride in ether yields 5,6,7,8-tetrahydro-α-5,5,8,8-pentamethyl-2-naphthalene-methanol which is converted by treatment with phosphorus tribromide in ether/hexane in the presence of a small amount of pyridine into 2-bromoethyl-5,6,7,8-tetrahydro-5,5,8,8-tetramethyl-naphthalene. This bromoethyl compound is converted by treatment with triphenylphosphine in xylene while heating for 12 hours into [1-(5,6,7,8-tetrahydro-5,5,8,8-tetramethyl-2-naphthyl)-ethyl]-triphenylphosphonium bromide which, in a Wittig reaction with 4-ethoxycarbonyl-benzaldehyde, yields p-[(E)-2-(5,6,7,8-tetrahydro-5,5,8,8-tetramethyl-2-naphthyl)-propenyl]-benzoic acid ethyl ester of melting point 90°-91° C. This ester is reduced with lithium aluminum hydride in ether/tetrahydrofuran to give p-[(E)-2-(5,6,7,8-tetrahydro-5,5,8,8-tetramethyl-2-naphthyl)-propenyl]-benzyl alcohol of melting point 123°-124° C. (from methanol).

A mixture of 5 g of the foregoing alcohol, 6.3 g of 2,3,4,6-tetra-O-acetyl-α-D-glucopyranosyl bromide and 1.5 g of mercuric cyanide is heated to reflux in 250 ml of toluene for 5 hours. The salts are filtered off and the solution is washed with saturated sodium hydrogen carbonate solution and water, dried and evaporated. Recrystallisation from methanol yields p-[(E)-2-(5,6,7,8-tetrahydro-5,5,8,8-tetramethyl-2-naphthyl)-propenyl]-benzyl-2,3,4,6-tetra-O-acetyl-β-D-glucopyranoside of melting point 134°-135° C. (from methanol).

EXAMPLE 5

A solution of 2.8 g of methyl [p-[(E)-2-(5,6,7,8-tetrahydro-5,5,8,8-tetramethyl-2-naphthyl)-propenyl]-benzyl-2,3,4-tri-O-acetyl-β-D-glucopyranoside]-uronate in 100 ml of methanolic ammonia (almost saturated at 0° C.) was left to stand at room temperature and then evaporated. Recrystallisation from ethanol yielded p-[(E)-2-(5,6,7,8-tetrahydro-5,5,8,8-tetramethyl-2-naphthyl)-propenyl]-benzyl-β-D-glucopyranoside-uronamide of melting point 194° C.; $[\alpha]_D^{25} = -38°$ (c=1 in pyridine).

EXAMPLE 6

From p-[(E)-2-(5,6,7,8-tetrahydro-5,5,8,8-tetramethyl-2-naphthyl)-propenyl]-benzyl alcohol and methyl 2,3,4-tri-O-acetyl-α-D-glucopyransyl bromide uronate there was obtained methyl [p-[(E)-2-(5,6,7,8-tetrahydro-5,5,8,8-tetramethyl-2-naphthyl)-propenyl]-benzyl-2,3,4-tri-O-acetyl-β-D-glucopyranoside]-uronate of melting point 162°-163° C. (from ethanol); $[\alpha]_D^{25} = -59.7°$ (c=1 chloroform).

EXAMPLE 7

In a manner analogous to that described in Example 4, from methyl [p-[(E)-2-(5,6,7,8-tetrahydro-5,5,8,8-tetramethyl-2-naphthyl)-propenyl]-benzyl-2,3,4-tri-O-acetyl-β-d-glucopyranoside]-uronate there was obtained methyl [p-[(E)-2-(5,6,7,8-tetrahydro-5,5,8,8-tetramethyl-2-naphthyl)-propenyl]-benzyl-β-D-glucopyranoside]-uronate of melting point 103°-104° C. (with decomposition, from ispropyl ether); $[\alpha]_D^{25} = -65.6°$ (c=1 in chloroform).

EXAMPLE 8

1.9 g of methyl [p-[(E)-2-(5,6,7,8-tetrahydro-5,5,8,8-tetramethyl-2-naphthyl)-propenyl]-benzyl-β-D-glucopyranoside]-uronate were heated to reflux for 1 hour in 190 ml of methanol with 10.8 ml of 1 N methanolic sodium hydroxide. After adding 2-propanol until turbidity occurred and cooling, there crystallised sodium p-[(E)-2-(5,6,7,8-tetrahydro-5,5,8,8-tetramethyl-2-naphthyl)-propenyl]-benzyl-β-D-glucopyranoside-uronate of melting point 240°-242° C. (with decomposition); $[\alpha]_D^{25} = -44.1°$ (c=1 in water).

Methyl [p-[(E)-2-(5,6,7,8-tetrahydro-5,5,8,8-tetramethyl-2-naphthyl)-propenyl]-benzyl-β-D-glucopyranoside]-uronate was heated to reflux for 1 hour in 430 ml of methanol with 24.5 ml of 1 N methanolic sodium hydroxide. The residue was dissolved in 100 ml of water, the solution was neutralised with Amberlite IR-120 (hydrogen ion form) resin and freeze-dried. There was obtained p-[(E)-2-(5,6,7,8-tetrahydro-5,5,8,8-tetramethyl-2-naphthyl)-propenyl]-benzyl-β-D-glucopyranoside-uronic acid of melting point 174°-175° C. (with decomposition, from methanol/benzene); $[\alpha]_D^{25} = -28°$ (c=1 in pyridine).

EXAMPLE A

Capsules for oral administration can contain the following ingredients:

| | Per capsule |
|---|---|
| Methyl 2,6-bis-O-[p-[(E)-2- | |

| | Per capsule |
|---|---|
| (5,6,7,8-tetrahydro-5,5,8,8-tetramethyl-2-naphthyl)-propenyl]-benzoyl]-α-D-glucopyranoside | 0.1 mg |
| Wax mixture | 50.5 mg |
| Vegetable oil | 98.9 mg |
| Trisodium salt of ethylenediamine-tetraacetic acid | 0.5 mg |

EXAMPLE B

| Methyl 2,6-bis-O-[p-[(E)-2-(5,6,7,8-tetrahydro-5,5,8,8-tetramethyl-2-naphthyl)-propenyl]-benzoyl]-α-D-glucopyranoside | 0.1 g |
|---|---|
| Vaseline (white) | 35.0 g |
| Wax (white) | 10.0 g |
| Paraffin oil (viscous) | 18.0 g |
| DEHYMULS E* | 7.0 g |
| Benzoic acid (pure) | 0.2 g |
| Deionised water | ad 100.0 g |

EXAMPLE C

| Methyl 2,6-bis-O-[p-[(E)-2-(5,6,7,8-tetrahydro-5,5,8,8-tetramethyl-2-naphthyl)-propenyl]-benzoyl]-α-D-glucopyranoside | 0.03 g |
|---|---|
| Vaseline (white) | 35.0 g |
| Wax (white) | 10.0 g |
| Paraffin oil (viscous) | 18.0 g |
| DEHYMULS E* | 7.0 g |
| Benzoic acid (pure) | 0.2 g |
| Deionised water | ad 100.0 g |

*High molecular weight aliphatic ester; supplier: Deutsche Hydriewerke.

We claim:
1. Compounds of the general formula:

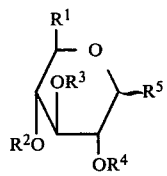

where $R^1$ represents a group of the formula —$CH_2OH$, —$CH_2OR^6$, —$COR^7$ or —$CONH_2$; $R^2$ represents hydrogen or lower alkanoyl; $R^3$ and $R^4$ represent hydrogen or lower alkanoyl or a group $R^6$; $R^5$ represents lower alkoxy or a group of the formula $OR^6$ or $OR^8$; $R^6$ represents a group of the formula:

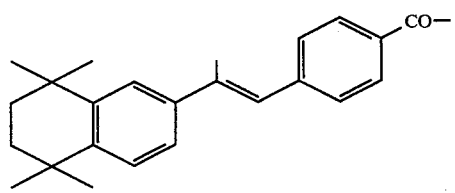

$R^7$ represents hydroxy, lower alkoxy or OM in which M represents a cation; and $R^8$ represents a group of the formula:

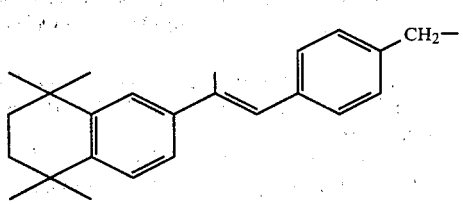

providing that: (i) $R^1$ represents a group of the formula —$CH_2OR^6$; $R^2$ represents hydrogen and one of $R^3$ and $R^4$ hydrogen and the other represents a group $R^6$ when $R^5$ represents lower alkoxy; (ii) $R^1$ represents a group of the formula —$COR^7$ and $R^2$, $R^3$ and $R^4$ represent lower alkanoyl when $R^5$ represents a group of the formula $OR^6$; or (iii) $R^1$ represents a group of the formula —$CH_2OH$, —$COR^7$ or —$CONH_2$ and $R^2$, $R^3$ and $R^4$ represent hydrogen of lower alkanoyl when $R^5$ represents a group of the formula $OR^8$; and the pharmaceutically acceptable acid addition salts thereof.

2. Compounds according to claim 1 wherein the compound has formula:

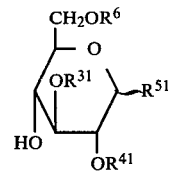

wherein $R^{51}$ represents lower alkoxy and one of $R^{31}$ and $R^{41}$ represents a group $R^6$ as defined in claim 1 and the other represents hydrogen.

3. Compounds in accordance with claim 1 of the general formula:

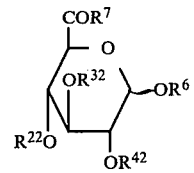

wherein $R^{22}$, $R^{32}$ and $R^{42}$ represent lower alkanoyl and $R^6$ and $R^7$ are as defined in claim 1.

4. Compounds according to claim 1 wherein the compound has the general formula:

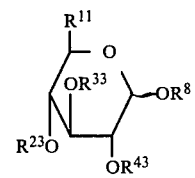

wherein $R^{11}$ represents a group of the formula —$CH_2OH$, —$COR^7$ or —$CONH_2$, $R^{23}$, $R^{33}$, $R^{43}$ represent hydrogen or lower alkanoyl and $R^8$ is as defined in claim 1.

5. Compounds according to claim 2, wherein $R^{51}$ represents methoxy.

6. Compounds according to claim 3, wherein $R^7$ represents methoxy.

7. Compounds according to claim 4, wherein $R^{11}$ represents a group of the formula —$CONH_2$ or —COONa.

8. Methyl 2,6-bis-0-[p-[(E)-2-(5,6,7,8-tetrahydro-5,5,8,8-tetramethyl-2-naphthyl)-propenyl]benzoyl]-α-D-glucopyranoside.

9. Methyl 2,3,4-tri-O-acetyl-1-O-[p-[(E)-2-(5,6,7,8-tetrahydro-5,5,8,8-tetramethyl-2-naphthyl)-propenyl]-benzoyl]-α-D-glucopyranuronate; methyl 2,3,4-tri-O-acetyl-1-O-[p-[(E)-2-(5,6,7,8-tetrahydro-5,5,8,8-tetramethyl-2-naphthyl)-propenyl]-benzoyl]-β-D-glucopyranuronate; methyl-3,6-bis-O-[p-[(E)-2-(5,6,7,8-tetrahydro-5,5,8,8,-tetramethyl-2-naphthyl)-propenyl]-benzoyl]-α-D-glucopyranoside; p-[(E)-2-(5,6,7,8,-tetrahydro-5,5,8,8,-tetramethyl-2-naphthyl)-propenyl]-benzyl-α-D-glucopyranoside; p-[(E)-2-(5,6,7,8-tetrahydro-5,5,8,8-tetramethyl-2-naphthyl)-propenyl]-benzyl-β-D-glucopyranoside-uronamide; methyl [p-[(E)-2-(5,6,7,8-tetrahydro-5,5,8,8-tetramethyl-2-naphthyl)-propenyl]-benzyl-2,3,4-tri-O-acetyl-β-D-glucopyranoside]-uronate; methyl [p-[(E)-2-(5,6,7,8-tetrahydro-5,5,8,8-tetramethyl-2-naphthyl)-propenyl]-benzyl-β-D-glucopyranoside]-uronate; sodium p-[(E)-2-(5,6,7,8-tetrahydro-5,5,8,8-tetramethyl-2-naphthyl)-propenyl]-benzyl-β-D-glucopyranoside-uronate or p-[(E)-2-(5,6,7,8-tetrahydro-5,5,8,8-tetramethyl-2-naphthyl)-propenyl]-benzyl-β-D-glucopyranoside-uronic acid.

* * * * *